United States Patent [19]

Sarantakis

[11] 4,061,608
[45] Dec. 6, 1977

[54] ARG⁴-SOMATOSTATIN AND ANALOGUES THEREOF

[75] Inventor: Dimitrois Sarantakis, West Chester, Pa.

[73] Assignee: American Home Products Corporation, New York, N.Y.

[21] Appl. No.: 705,721

[22] Filed: July 13, 1976

[51] Int. Cl.² .................... C08L 67/00; C07C 103/52
[52] U.S. Cl. .................................. 260/8; 260/112.5 S
[58] Field of Search ............................ 260/112.5 S, 8

[56] References Cited

U.S. PATENT DOCUMENTS 3,904,594  9/1975  Guillemin et al. ............ 260/112.5 S

OTHER PUBLICATIONS

Biochem. & Biophys.,Res. Comm. 65, 1975, pp. 746–750.
Biochem. & Biophys., Res. Comm. 54, 1973, pp. 234–237.

*Primary Examiner*—Delbert R. Phillips
*Attorney, Agent, or Firm*—Richard K. Jackson

[57] ABSTRACT

Polypeptides of the formula:

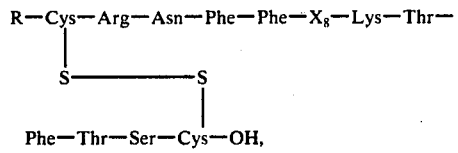

the linear precursors, intermediates and non-toxic acid addition salts thereof, wherein R is hydrogen or Ala-Gly and $X_8$ is L-Trp or D-Trp are described. These polypeptides inhibit the secretion of growth hormone and, at low doses, excel in their higher glucagon to insulin lowering ratio.

9 Claims, No Drawings

ARG 4-SOMATOSTATIN AND ANALOGUES THEREOF

DESCRIPTION OF THE INVENTION

In accordance with this invention there is provided a group of polypeptides of the following formula:

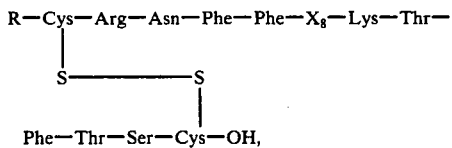

its linear precursor or a non-toxic acid addition salt thereof, in which R is hydrogen, or Ala-Gly and $X_8$ is L-Trp or D-Trp. These compounds inhibit the secretion of growth hormone and demonstrate very desirable selectivity at low doses in decreasing blood serum concentration of glucagon without materially lowering the concentration of insulin. Thus, the compounds of this invention are superior to somatostatin in the treatment of diabetes where the lowering of blood serum insulin concentrations is not desirable.

The intermediates produced in the synthesis of the polypeptides disclosed herein present an additional aspect of the invention. The intermediates are of the formula:

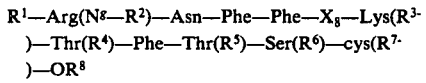

wherein $X^8$ is L-tryptophyl or D-tryptophyl;

$R^1$ is hydrogen or an α-amino protecting group;

$R^2$ is hydrogen, nitro, tosyl, benzyloxycarbonyl, adamantyloxycarbonyl or tert-butyloxycarbonyl;

$R^3$ is hydrogen, tosyl, t-amyloxycarbonyl, t-butyloxycarbonyl, diisopropyloxycarbonyl, benzyloxycarbonyl, halobenzyloxycarbonyl or nitrobenzyloxycarbonyl;

$R^4$, $R^5$ and $R^6$ are hydrogen or, independently, acetyl, benzoyl, tert-butyl, benzyl;

$R^7$ is benzyl, trityl, benzyloxycarbonyl, benzhydryl, tetrahydropyranyl, acetamidomethyl, benzoyl, benzylthiomethyl, ethylcarbamoyl, thioethyl, S-sulfonate salt, 3,4-dimethylbenzyl, p-methoxybenzyl or p-nitrobenzyl; and $R^8$ is hydrogen or —CH$_2$-[polystyrene resin support]

The polypeptide intermediates and final products are produced by the well known solid phase method as described by Stewart et al., Solid Phase Peptide Synthesis, Freeman and Co., San Francisco, 1969. As applied to the compounds of this invention, α-amino and sulfhydryl protected cysteine is attached to a chloromethylated polystyrene resin followed by removal of the α-amino protecting group with trifluoroacetic acid in methylene chloride, trifluoroacetic acid alone or HCl in dioxane. The deprotection is conducted at a temperature between about 0° C. and room temperature. Other standard cleaving reagents and conditions for removal of specific α-amino protecting groups may be used as described in Schroder E. Lubke, "The Peptides", 1, 72–75 (Academic Press, 1965). After removal of the α-amino protecting group the subsequent protected amino acids are coupled individually to the resin supported sequence, seriatim. Alternatively, small peptide fragments may be prepared by the solution method and introduced into the solid phase reactor in the desired order. Each protected amino acid or amino acid sequence is introduced into the solid phase reactor in about a four fold excess. The coupling is carried out in dimethylformamide, methylene chloride, or a mixture of the two solvents. The success of each coupling reaction at each stage of the synthesis is determined by the ninhydrin reaction as described by E. Kaiser et al., Analyt. Biochem., 34, 595 (1970). Where incomplete coupling has occurred, the reaction is repeated before the α-amino protecting group is removed for introduction of the next amino acid or amino acid sequence.

The coupling reagents employed were 1-hydroxybenzotriazole and diisopropylcarbodiimide.

After the desired amino acid sequence has been synthesized, the polypeptide is removed from the resin support by treatment with hydrogen fluoride and anisole to obtain the fully deprotected linear polypeptide. The cyclic disulfide is produced by air oxidation.

Non-toxic acid addition salts of the linear and cyclic polypeptides are produced by methods well known in the art from hydrochloric, hydrobromic, sulfuric, phosphoric, polyphosphoric, maleic, acetic, citric, benzoic, succinic, malonic or ascorbic acid and the like.

The protecting groups employed throughout the solid phase synthesis are well known to the art. The α-amino protecting groups employed with each amino acid introduced in sequence of the ultimate polypeptide are of the (1) acyl type protecting groups illustrated by the following: formyl, trifluoracetyl, phthalyl, p-toluenesulfonyl (tosyl), nitrophenylsulfenyl, etc.; (2) aromatic urethane type protecting groups illustrated by benzyloxycarbonyl and substituted benzyloxycarbonyl such as p-chlorobenzyloxycarbonyl, p-nitrobenzyloxycarbonyl, p-bromobenzyloxycarbonyl, p-methoxybenzyloxycarbonyl; (3) aliphatic urethane protecting groups illustrated by tert-butyloxycarbonyl, diisopropylmethoxycarbonyl, isopropyloxycarbonyl, allyloxycarbonyl, 2,2,2-tri=chloroethoxycarbonyl, amyloxycarbonyl; (4) cycloalkyl urethane type protecting groups illustrated by cyclopentyloxycarbonyl, adamantyloxycarbonyl, cyclohexyloxycarbonyl; (5) thio urethane type protecting groups such as phenylthiocarbonyl; (6) alkyl type protecting groups as illustrated by triphenylmethyl (trityl); (7) trialkylsilane groups such as trimethylsilane. The preferred α-amino protecting group defined by R is tert-butyloxycarbonyl;

The side chain nitrogen atoms of arginine, denoted $N^g$ are protected by a group $R^2$ which may be nitro, tosyl, benzyloxycarbonyl, adamantyloxycarbonyl or tert-butyloxycarbonyl, preferably the tosyl group. Protection via the nitro or tosyl group is on either the $N^\omega$ or $N^{\omega'}$ nitrogen atoms, while the oxycarbonyl type protecting groups protect the $N^\delta$ and either one of the $N^\omega$ or $N^{\omega'}$ nitrogen atoms.

Protection for the side chain amino group of lysine, depicted as $R^3$, may be by tosyl, t-amyloxycarbonyl, t-butyloxycarbonyl, diisopropyloxycarbonyl, benzyloxycarbonyl, halobenzyloxycarbonyl, nitrobenzyloxycarbonyl, and the like, the 2-chlorobenzyloxycarbonyl group being preferred.

Protection for the hydroxyl group of threonine and serine as depicted by $R^4$, $R^5$, and $R^6$, may be with the acetyl, benzoyl, tert-butyl, benzyl. The benzyl group is preferred for this purpose.

The protecting group for the sulfhydryl group of the cysteinyl amino acid residue illustrated by $R^7$ is a group selected from the class consisting of benzyl; substituted benzyl wherein the substituent is at least one of methyl, methoxy, nitro, or halo (e.g. 3,4-dimethylbenzyl, p-methoxybenzyl, p-chlorobenzyl, p-nitrobenzyl, etc); trityl, benzyloxycarbonyl, benzhydryl, p-methoxybenzyloxycarbonyl, benzylthiomethyl, ethylcarbamoyl, thioethyl, tetrahydropyranyl, acetamidomethyl, benzoyl, s-sulfonate salt, etc; the p-methoxybenzyl group being preferred.

In selecting a particular side chain protecting group to be used in the synthesis of the peptides of this invention, the following rules should be followed: (a) The side chain protecting group must be stable to the reagent and under the reaction conditions selected for removing the α-amino protecting group at each step of the synthesis, (b) the protecting group must retain its protecting properties (i.e. not be split off under coupling conditions), and (c) the side chain protecting group must be removable upon the completion of the synthesis containing the desired amino acid sequence under reaction conditions that will not alter the peptide chain.

The following Example illustrates the preparative technique applicable in the production of the compounds of this invention. By introducing tert-butyloxycarbonyl protected D-tryptophan into the solid phase reactor as the seventh amino acid introduced, the compounds corresponding to D-Trp as $X_8$ in the generic formula, supra, are produced. The fully protected intermediate containing the D-Trp unit, corresponding to the illustrative compound prepared in the following example, is: α-tert-butyloxycarbonyl-S-p-methoxybenzyl-L-cysteinyl-N$^g$-tosyl-L-arginyl-L-asparaginyl-L-phenylalanyl-L-phenylalanyl-D-tryptophyl-ε-2chlorobenzyloxycarbonyl-L-lysyl-O-benzyl-L-threonyl-L-phenylalanyl-O-benzyl-L-threonly-O-benzyl-L-seryl-S-p-methoxybenzyl-L-cysteinyl-hydroxymethyl-polystyrene.

Likewise, the sequential introduction of t-butyloxycarbonyl-Gly-OH as the thirteenth amino acid and t-butyloxycarbonyl-Ala-OH as the fourteenth member of the sequence affords, after complete deprotection, a tetradecapeptide of the formula:

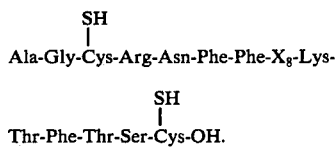

in which $X_8$ is L-Trp or D-Trp and all other optically active amino acids are of the L-series, which linear intermediate readily cyclized under mild air oxidation.

α-tert-butyloxycarbonyl-S-p-methoxybenzyl-L-cysteinyl-N$^g$-tosyl-L-arginyl-L-asparaginyl-L-phenylalanyl-L-phenylalanyl-L-tryptophyl-ε-2-chlorobenzyloxy-carbonyl-L-lysyl-O-benzyl-L-threonyl-L-phenylalanyl-O-benzyl-L-threonyl-O-benzyl-L-servi-S-p-methoxybenzyl-L-cysteinyl-hydroxymethyl-polystyrene A solution of the cesium salt of t-butyloxycarbonyl-S-p-methoxybenzyl-L-cysteine (25mmoles) in dimethylformamide is stirred with chloromethylated polystyrene resin (30 g) at 50° C for 16 hours. The resin is filtered and washed with dimethylformamide, 10% water in dimethylformamide, ethanol and dimethylformamide (1:9), dimethylformamide, methylene dichloride and methanol. The amino acid resin after drying in vacuo over KOH is found to be substituted to the extent of 0.40 mmoles of cysteine per gram of resin. Eight grams of this polymeric ester is treated according to schedule A for the incorporation of, tert-butyloxycarbonyl-Ser(benzyl)-OH, tert-butyloxycarbonyl-Thr(benzyl)-OH, tert-butyloxycarbonyl-Phe-OH, tert-butyloxycarbonyl-Thr-(benzyl)OH, tert-butyloxycarbonyl-Lys(2-chlorobenzyloxycarbonyl)OH, tert-butyloxycarbonyl-TrpOH, tert-butyloxycarbonyl-Phe-OH, tert-butyloxycarbonyl-Phe-OH, tert-butyloxycarbonyl-Asn-OH, tert-butyloxycarbonyl-Arg(tosyl)-OH and tert-butyloxycarbonyl-Cys(p-methoxybenzyl)-OH

Schedule A

1. Wash with $CH_2Cl_2 \times 3$
2. Treat with trifluoroacetic acid-$CH_2Cl_2$-1,2-ethane dithiol (1:1:0.5%) for 5 minutes
3. Treat with trifluoroacetic acid-$CH_2Cl_2$-1,2-ethane dithiol (1:1:0.5%) for 25 minutes.
4. Wash with $CH_2Cl_2 \times 3$
5. Wash with dimethylformamide
6. Treat with 12% triethylamine in dimethylformamide twice for 3 minutes
7. Wash with dimethylformamide
8. Wash with $CH_2Cl_2 \times 3$
9. Treat with 4 equivalents of the corresponding amino acid derivative and 4 equivalents of N-hydroxybenzotriazole in dimethylformamide—$CH_2Cl_2$ and stir for 5 minutes. In the case of tert-butyloxycarbonyl-Asn-OH, 8 equivalents of N-hydroxybenzotriazole are added.
10. Add in two portions 5 equivalents of N,N-diisopropylcarbodiimide dissolved in $CH_2Cl_2$ and over a period of 30 minutes. Reaction time-18 hours.
11. Wash with dimethylformamide × 3
12. Wash with $CH_2Cl_2 \times 3$
13. Test ninhydrin reaction according to Kaiser et al., Annal. Biochem. 34 595 (1970). In case of incomplete reactions repeat lines 9 to 13 as above.

The title peptido resin gave the following: Amino acid analysis Asp (1) 1.03, Thr(2) 1.93, Ser(1) 0.47, Cys(2) 1.43, Phe(3) 3, Lys(1) 0.99, $NH_3$(1) 2.87, Arg(1) 0.81.

L-Cysteinyl-L-arginyl-L-asparaginyl-L-phenylalanyl-L-phenylanalyl-L-tryptophyl-L-lysyl-L-threonyl-L-phenylalanyl-L-threonyl-L-seryl-L-cysteine (1–12 disulfide)

The peptidoresin of the previous paragraph (9.65 g) was treated with liquid hydrogen fluoride, ca. 120 ml, in the presence of 12 ml anisole for 1 hour in an ice-bath, then the excess hydrogen fluoride was removed in vacuo as fast as possible (ca. 90 minutes). The residue was extracted with aqueous acetic acid (ca. 15%) and the milky solution was washed with diethyl ether. The aqueous layer diluted to ca. 3,000 ml with deaerated water, the pH adjusted to 7.4 with dilute $NH_4OH$, and the solution was left to stand in the cold room for 2 days. The solution was acidified with glacial acetic acid to pH 6.5 and lyophilized to yield 2.6 g of solid. This solid was chromatographed through Sephadex G-10 (column, 2.5 × 90 cm) and eluted with 1 M-acetic acid. Fractions of 4.5 ml were collected. The fractions in tubes 48 to 107 were pooled and lyophilized to yield 1.2 g of solid which was chromatographed through Sephadex G-15 (column 2.5 × 150 cm) and eluted with 1 M-acetic acid. Fractions of 4 ml were collected and tubes 121–180 were pooled and lyophilized to yield 163.5 mg of the title deprotected dodecapeptide as the triacetate salt.

$R_f$ (n-butanol-water-glacial acetic acid, 4:5:1, v/v/v) 0.61

$R_f$ (n-butanol-water-glacial acetic acid-pyridine, 4.2:1:1, v/v/v/v) 0.71

$R_f$ (iso-amyl alcohol-pyridine-water, 7:7:6, v/v/v) 0.66

Amino acid analysis Asp (1) 0.96, Thr(2) 1.93, Ser(1) 0.95, Phe(3) 3, Lys(1) 0.98, Arg(1) 0.71.

The activity of the product of the preceding preparatory example (des-Ala$^1$,Gly$^2$)-Arg$^4$-Somatostatin was determined by the following procedure:

Albino male rats were administered Nembutal intraperitoneally at a dose of 50 milligrams per kilogram. Fifteen minutes later a subcutaneous injection of the test compound or physiological saline was administered. Ten minutes later 0.5 milliliters of arginine (300 milligrams per milliliter, pH 7.2) is injected into the heart. Five minutes after receipt of the arginine the rats are decapitated and blood is collected into trasylol-EDTA. Appropriate aliquots are assayed for growth hormone, glucagon and insulin concentrations.

The following data was obtained for the test compound (des-Ala$^1$, Gly$^2$)-Arg$^4$-Somatostatin;

|  | Dose µg/kg | GH ng/ml | INS. µU/ml | GLUC. pg/ml |
|---|---|---|---|---|
| test compound | 1500 | 14* | 106± | NA |
| Control | — | 165 | 168 |  |
| test compound | 400 | 10* | 144 | 11+ |
| Control | — | 187 | 173 | 18 |
| test compound | 200 | 87* | 107 | 4* |
| Control | — | 276 | 135 | 16 |

*p<0.01
+p<0.05
NA - not assayed

From this data, it is found that (des-Ala$^1$,Gly$^2$)-Arg$^4$-Somatostatin, administered in the range of about 200 to 400 µg/kg, suppresses growth hormone and glucagon markedly without drastically changing the insulin concentration, thereby providing a decided advantage in treatment of diabetes, where better blood glucose control may be obtained by avoiding insulin suppression.

The activity of (des-Ala$^1$, Gly$^2$)-Arg$^4$-Somatostatin is representative of the activity possessed by the structural analogue containing D-Trp$^8$ and Ala$^1$-Gly$^2$.

The compounds described herein may be administered to warm blooded mammals, including humans, either intravenously, subcutaneously, intramuscularly or orally to inhibit the release of growth hormone where the host being treated requires therapeutic treatment for excess secretion of somatotropin which is associated with conditions such as juvenile diabetes and acromegaly. The contemplated dose range for oral administration in tablet or capsule form to large mammals is about 0.015 mg to about 7 mg/kg of body weight per day while the dose range for intravenous injection is an aqueous solution is about 1.14 µg to about 0.15 mg/kg of body weight per day. When administered subcutaneously or intramuscularly a dose range of about 1.5 µg to about 7 mg/kg of body weight per day is contemplated. Obviously, the required dosage will vary with the particular condition being treated, the severity of the condition and the duration of treatment. If the active ingredient is administered in tablet form the tablet may contain: a binder such as gum tragacanth, corn starch, gelatin, an excipient such as dicalcium phosphate; a disintegrating agent such as corn starch, alginic acid, etc.; a lubricant such as magnesium stearate; and a sweetening and/or flavoring liquid carriers for intravenous administration include isotonic saline, phosphate buffer solutions, etc.

What is claimed is:

1. A polypeptide of the formula:

$$R-Cys-Arg-Asn-Phe-Phe-X_8-Lys-Thr-$$
$$\quad \ \ |\text{_____}|$$
$$\quad \ \ S\qquad\qquad\quad\ S$$
$$\qquad\qquad\qquad\qquad\ |$$
$$Phe-Thr-Ser-Cys-OH,$$

its linear precursor or a non-toxic acid addition salt thereof, in which
R is hydrogen or Ala-Gly-
and
$X_8$ is L-Trp or D-Trp.

2. A polypeptide of claim 1 of the formula:

$$Ala-Gly-Cys-Arg-Asn-Phe-Phe-X_8-Lys-Thr-$$
$$\qquad\qquad\quad\ |\text{_____}|$$
$$\qquad\qquad\quad\ S\qquad\qquad\ S$$
$$\qquad\qquad\qquad\qquad\qquad\ |$$
$$Phe-Thr-Ser-Cys-OH,$$

its linear precursor or a non-toxic acid addition salt thereof, in which
$X_8$ is L-Trp or D-Trp.

3. A polypeptide of claim 1 of the formula:

$$H-Cys-Arg-Asn-Phe-Phe-X_8-Lys-Thr-$$
$$\quad\ \ |\text{_____}|$$
$$\quad\ \ S\qquad\qquad\ S$$
$$\qquad\qquad\qquad\ \ |$$
$$Phe-Thr-Ser-Cys-OH,$$

its linear precursor or a non-toxic acid addition salt thereof, in which
$X_8$ is L-Trp or D-Trp.

4. The polypeptide of claim 3 which is L-cysteinyl-L-arginyl-L-asparaginyl-L-phenylalanyl-L-phenylalanyl-L-tryptophyl-L-lysyl-L-threonyl-L-phenylalanyl-L-threonyl-L-seryl-L-cysteine or a non-toxic acid addition salt thereof.

5. The polypeptide of claim 3 which is L-cysteinyl-L-arginyl-L-asparaginyl-L-phenylalanyl-L-phenylalanyl-L-tryptophyl-L-lysyl-L-threonyl-L-phenylalanyl-L-threonyl-L-seryl-L-cysteine (cyclic 1,12 disulfide) or a non-toxic acid addition salt thereof.

6. A polypeptide of the formula:

$R^1$—Arg($N^g$—$R^2$)—Asn—Phe—Phe—$X_8$—Lys($R^3$)—Thr($R^4$)—Phe—Thr($R^5$)—Ser($R^6$)—Cys($R^7$)—OR$^8$ wherein
$X_8$ is L-tryptophyl or D-tryptophyl;
$R^1$ is hydrogen or an α-amino protecting group;

$R^2$ is hydrogen, nitro, tosyl, benzyloxycarbonyl, adamantyloxycarbonyl or tert-butyloxycarbonyl;

$R^3$ is hydrogen, tosyl, t-amyloxycarbonyl, t-butyloxycarbonyl, diisopropyloxycarbonyl, benzyloxycarbonyl, halobenzyloxycarbonyl or nitrobenzyloxycarbonyl;

$R^4$, $R^5$ and $R^6$ are hydrogen or, independently, acetyl, benzoyl, tert-butyl, benzyl;

$R^7$ is benzyl, trityl, benzyloxycarbonyl, benzhydryl, tetrahydropyranyl, acetamidomethyl, benzoyl, benzylthiomethyl, ethylcarbamoyl, thioethyl, S-sulfonate salt, 3,4-dimethylbenzyl, p-methoxybenzyl or p-nitrobenzyl; and $R^8$ is hydrogen or —$CH_2$-[polystyrene resin support].

7. A polypeptide of claim 6 in which $R^1$ is tert-butyloxycarbonyl.

8. A polypeptide of claim 6 in which $R^1$ is hydrogen.

9. A polypeptide of claim 6 in which
$R^1$ is tert-butyloxycarbonyl
$R^2$ is tosyl
$R^3$ is 2-chlorobenzyloxycarbonyl
$R^4$, $R^5$, and $R^6$ are benzyl
$R^7$ is p-methoxybenzyl
$R^8$ is —$CH_2$-[polystyrene resin support].

* * * * *